United States Patent

Oi et al.

[11] Patent Number: 6,063,097
[45] Date of Patent: May 16, 2000

[54] SUPPORTING ELEMENT FOR STAPLE REGION

[75] Inventors: Shigeo Oi; Hiroshi Ohshima; Satoshi Hashimoto, all of Ayabe, Japan

[73] Assignee: Gunze Limited, Ayabe, Japan

[21] Appl. No.: 09/096,459

[22] Filed: Jun. 11, 1998

Related U.S. Application Data

[62] Division of application No. 08/825,457, Mar. 28, 1997, Pat. No. 5,814,057, which is a continuation of application No. 08/456,574, Jun. 1, 1995, abandoned, which is a continuation-in-part of application No. 08/434,989, May 4, 1995, abandoned.

[30] Foreign Application Priority Data

Jun. 3, 1994  [JP]  Japan ................................. 6-156353

[51] Int. Cl.⁷ .................................................. A61B 17/04
[52] U.S. Cl. ...................... 606/151; 227/178.1; 227/180.1
[58] Field of Search .................................. 606/151, 139; 227/175–180.2

[56] References Cited

U.S. PATENT DOCUMENTS

| | | |
|---|---|---|
| 4,397,311 | 8/1983 | Kanshin et al. ...................... 227/176.1 |
| 4,428,375 | 1/1984 | Ellman ..................................... 606/151 |
| 4,452,225 | 6/1984 | Usher ....................................... 606/151 |
| 4,548,202 | 10/1985 | Duncan .................................... 606/220 |
| 5,263,629 | 11/1993 | Trumbull et al. ....................... 606/151 |
| 5,327,914 | 7/1994 | Shlain . | |
| 5,370,650 | 12/1994 | Tovey et al. ............................. 606/151 |
| 5,397,324 | 3/1995 | Carroll et al. ........................ 227/178.1 |
| 5,441,193 | 8/1995 | Gravener ................................. 606/151 |
| 5,441,299 | 8/1995 | Lauritzen et al. .................... 280/728.2 |
| 5,447,940 | 9/1995 | Harvey et al. ........................... 514/310 |
| 5,503,638 | 4/1996 | Cooper et al. ........................... 606/151 |
| 5,542,594 | 8/1996 | McKean et al. ....................... 227/178.1 |

*Primary Examiner*—Gary Jackson
*Attorney, Agent, or Firm*—Armstrong, Westerman, Hattori, McLeland & Naughton

[57] ABSTRACT

A supporting element for a staple region suitable for application by an automatic stapling device employed during surgery. The supporting element comprises a fabric-like object having a tube-like shape, the supporting element in one end having a narrowed opening formed by stitching up with sewing yarn.

8 Claims, 6 Drawing Sheets

SUPPORTING ELEMENT FOR STAPLE REGION

This application is a divisional of Ser. No. 08/825,457 filed Mar. 28, 1997, now U.S. Pat. No. 5,814,057, which is a continuation of Ser. No. 08/456,574 filed Jun. 1, 1995, now abandoned; which is a continuation in part of Ser. No. 08/434,989 filed May 4, 1995, now abandoned.

FIELD OF THE INVENTION

The present invention relates to a provision of a supporting element for staple region. The element is suitable for application to an automatic stapling device.

BACKGROUND OF THE INVENTION

A stapler-type automatic stapling device in which a number of staples are laid has been frequently employed in surgeries such as ablation or anastomosis of lumina. When the stapling device is applied to surgery in lung, etc., an air-leakage problem at staple region may arise. In addition, when applied to soft tissues, problems of damage or rupture of tissues may arise.

It is an object of the invention to provide a novel supporting element for staple region suitable for application to an automatic stapling device. The supporting element for staple region is improved in ease of fitting and register, in prevention of misregister after fitting and in ease of cutting operation with cutter.

DISCLOSURE OF THE INVENTION

Figure 1:
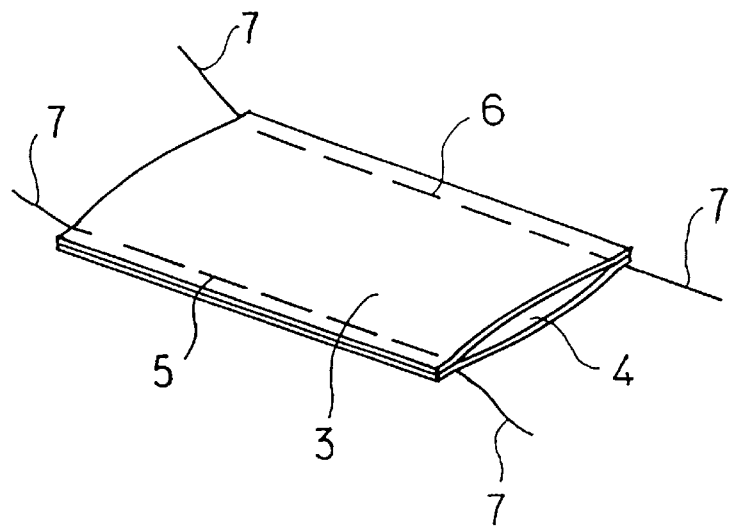
FIG. 1 is a diagonal view showing a supporting element for staple region of the invention.

The present invention provides a supporting element for staple region comprising a fabric-like object having a tube-like shape.

In addition, the present invention provides a tube-like supporting element for staple region, wherein said supporting element at one end has a narrowed opening formed by stitching up with sewing yarn.

In addition, the present invention provides a tube-like supporting element for staple region comprising a fabric-like object made of biodegradable and bioabsorbable material integrated with stretchable textile at both ends (hereinafter referred to as "invention I").

Further, the present invention provides a tube-like supporting element for staple region comprising a fabric-like object made of biodegradable and bioabsorbable material (hereinafter referred to as "invention II").

The invention relates to a tube-like supporting element for staple region. According to invention I, a part of the supporting element is composed of stretchable material to facilitate fitting of the supporting element on an automatic stapling device because of strechability thereof, to prevent misregister because of increased fitting properties, and to facilitate and ensure cutting the supporting element together with affected part because of tension of the supporting element.

According to invention II, the whole supporting element is made of biodegradable and bioabsorbable material to eliminate the need of removing non-biodegradable material after surgical operation and to prevent an accident letting foreign matter remain in the body due to failure of removing the non-biological material.

"Tube-like" means that both ends of fabric-like object or each end of fabric-like object and stretchable textile are integrated. A tube-like shape includes cylinder, prism, plane, etc.

The biodegradable and bioabsorbable material of the invention employed as a whole or part of the supporting element for staple region is characterized in that the material does not remains in vivo for a long period of time as foreign matter.

The stretchable textile of the invention I is prepared by knitting or weaving rubber threads, polyurethane elastic threads, crimped threads and bulky yarns, etc. in the weave thereof and has stretchability in lengthwise and crosswise directions. Although the weave is not specifically limited to, a stretch warp knit (power net) produced by interweaving polyurethane threads covered by nylon threads is preferably exemplified in view of ease of integration by sewing, etc., and stability of shape.

Examples of the fabric-like object made of biodegradable and bioabsorbable material are knitted fabric, woven fabric, unwoven fabric, film, etc. made of polyglycolic acid, polylactic acid, copolymer or mixture of polylactic acid and polyglycolic acid, para-dioxanone, polycaprolactone, chitin and like matters already applied to biomedical materials. Suitable material in view of flexibility, breathability, moderate nerve, thickness, blood absorbing properties, ease of passing of staples and degradability is unwoven fabric prepared by needle punching knit fabric or woven textile made of polyglycolic acid as disclosed in Japanese Examined Patent Publication No. 5-18579 and Japanese Unexamined Patent Publication No. 5-79586 by the applicant. The unwoven fabric has poor stretchability.

In carrying out the invention I, integration of said fabric-like object with stretchable textile is conducted by piling both materials (preferably the same size for workability of integration) cut in a desired size and integrating the both ends (both selvages) by sewing, adhesion, etc. An example of particularly preferable means for integration is plain stitch with sewing yarn in rough stitch to facilitate separation of both after fixation by staples. The ends of thread are preferably extended outside in a suitable length to facilitate the separation mentioned above. The sewing yarn includes sewing thread, suture, etc. The sewing yarn is composed of any material including nylon, polyester, vinylon, cotton, silk and like non-biodegradable polymer and above-mentioned biodegradable and bioabsorbable material. The sewing yarn is preferably made of the same biodegradable and bioabsorbable material of the invention, since the sewing yarn may be put together with the supporting element and remain in vivo. Further, it is important to accomplish said object that inner diameter of tube-like supporting element formed by said integration is the same as or smaller than outer diameter of stapling device applied to. Therefore, the size and shape of fabric-like object employed and sewing means for integration are preferably adapted to the object.

In carrying out the invention II, tube formation of fabric-like object made of biodegradable and bioabsorbable material is conducted by joining both ends of fabric-like object cut in a suitable size for adaptation of region inserted of staple of automatic stapling device using any method, such as rough stitch sewing, adhesion, etc. Temporary sewing and temporary adhesion are, in particular, preferable to improve workability after sewing process mentioned below. Tubular knitted textiles may be employed as tube-like supporting element for staple region.

Examples of automatic stapling devices are AUTOSUTURE MULTIFIRE GIA 80, 60 TYPE (trademark; product of UNITED STATE SURGICAL CO., LTD.), PROXIMATE LINEAR CUTTER 75, 55 TYPE (trade mark; product of ETHICON endo SURGERY CO., LTD.). For application to the automatic stapling devices, the supporting elements of the invention are simply fitted on staple built-in type cartridge section and frame section provided with slot for staple.

The fabric-like object may be composed of at least one material selected from the group consisting of non-biodegradable and non-bioabsorbable polymer such as nylon, polyester, vinylon, cotton, silk, etc.; biodegradable and bioabsorbable polymer such as polyglycolic acid, polylactic acid, copolymer or mixture of polylactic acid and polyglycolic acid, para-dioxanone, polycaprolactone, chitin, etc. The fabric-like object may be knitted fabric, woven fabric, unwoven fabric, film, etc.

EXAMPLE

The present invention will be described in detail with examples and drawings.

Example 1

FIG. 1 discloses a supporting element for staple region of the invention. The supporting element comprises unwoven fabric (3) made of biodegradable and bioabsorbable material, which is integrated with stretch warp knit (4) at both selvage by plain stitch with sutures (5), (6) as sewing yarn. The both ends of sutures (7), (7) are extended outside.

The unwoven fabric (3) is obtained by piling 4 sheets of cylindrical knitted webs having a weight per area of 45 g/m$^2$ which are needle-punched lightly along wales direction in conditions that the wales direction of one fabric and the course direction of the adjacent sheet are aligned, followed by needle-punching the piled webs. The cylindrical knitted webs are obtained by knitting threads of 12 filaments and 33 deniers made of polyglycolic acid with circular knitting machine (18 gauge). The stretch warp knit (4) having stretch warp knit weaves are prepared by interweaving polyurethane threads of 280 deniers and nylon fiber of 24 filaments and 70 deniers in a proportion of polyurethane:nylon=15:85 with warp knitting machine. Example of suture is polyglycilic acid suture of 4-0 size.

Said unwoven fabric (3) and stretch warp knit (4) are cut in the same size of 80×25 mm, piled, and then plain stitch with hand at a position 2 mm inner from side edge in a sewing pitch of 10 mm to form the tube-like supporting element for staple region (1) of the invention. Both ends of sutures (7) are extended outside about 8 cm in long. The same procedure is repeated except that the fabrics cut are 80×20 mm in size to give another supporting element for staple region (2).

Figure 2:
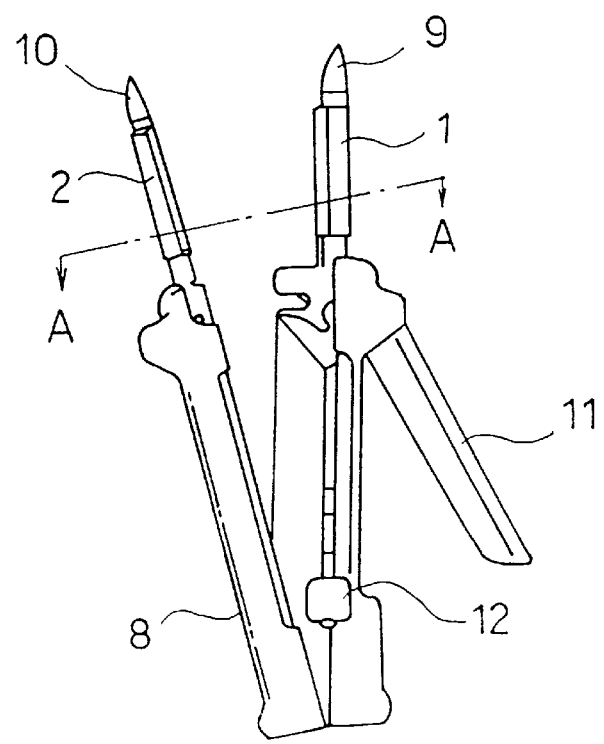
FIG. 2 is a front view showing the supporting element for staple region of FIG. 1 fitted on an automatic stapling device.
Figure 3:
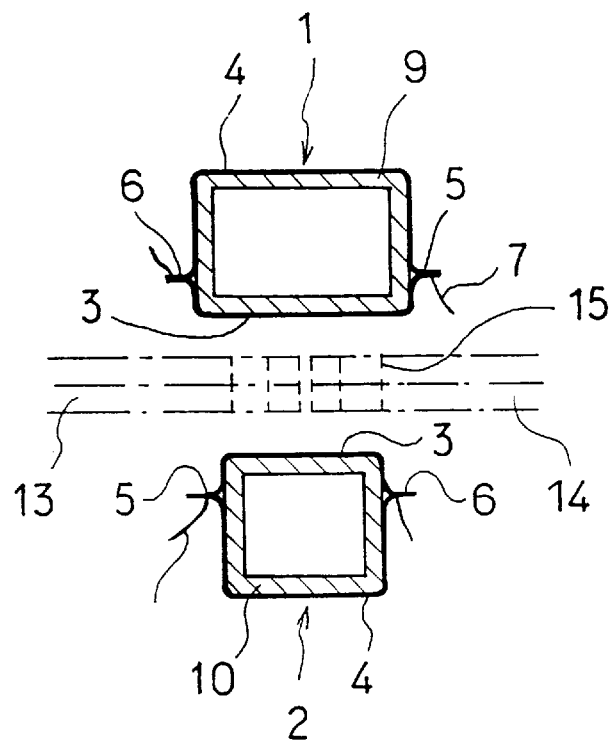
FIG. 3 is an A—A sectional view in FIG. 2.

FIG. 2 discloses a conventionally employed double staple-type automatic stapling device (8) provided with staple built-in-type cartridge section (9) and frame section (10) provided with slot for staple. The cartridge section and frame section are fitted with the supporting elements for staple region (1), (2). In FIG. 2, (11) corresponds to a handle for clamping body tissue and (12) corresponds to a lever having combined uses of cutter and stapler. When the lever (12) is raised, body tissue clamped is stapled and then cut. FIG. 3 is an A—A sectional view in FIG. 2. In FIG. 3, stretch warp knit (4) is fitted in an extended state.

Figure 4:
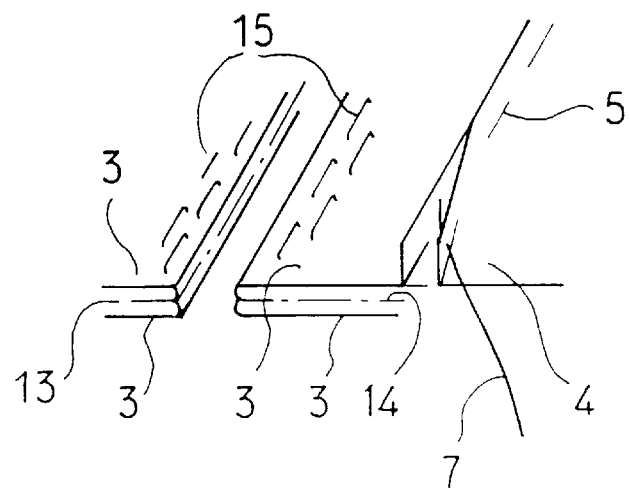
FIG. 4 is a diagonal view showing a supporting element for staple region of FIG. 1 when applied to a tissue in the body and operated.

As shown in FIGS. 3 and 4, during operation, an affected part of tissue in the body is sandwiched between unwoven fabrics (3), (3) of the supporting element fitted on cartridge section (9) and frame section (10) by clamping the handle (11). The affected tissue and unwoven fabrics are fixed together by raising the lever (12). The affected part (13) and normal part (14) of the tissue are separated with cutter by further raising the lever (12). The end (7) of suture is pulled to separate section remained in vivo (14) and section removed. The affected part (13) cut and stretchable fabric, i.e., stretch warp knit (4), are removed outside the body.

Figure 7:
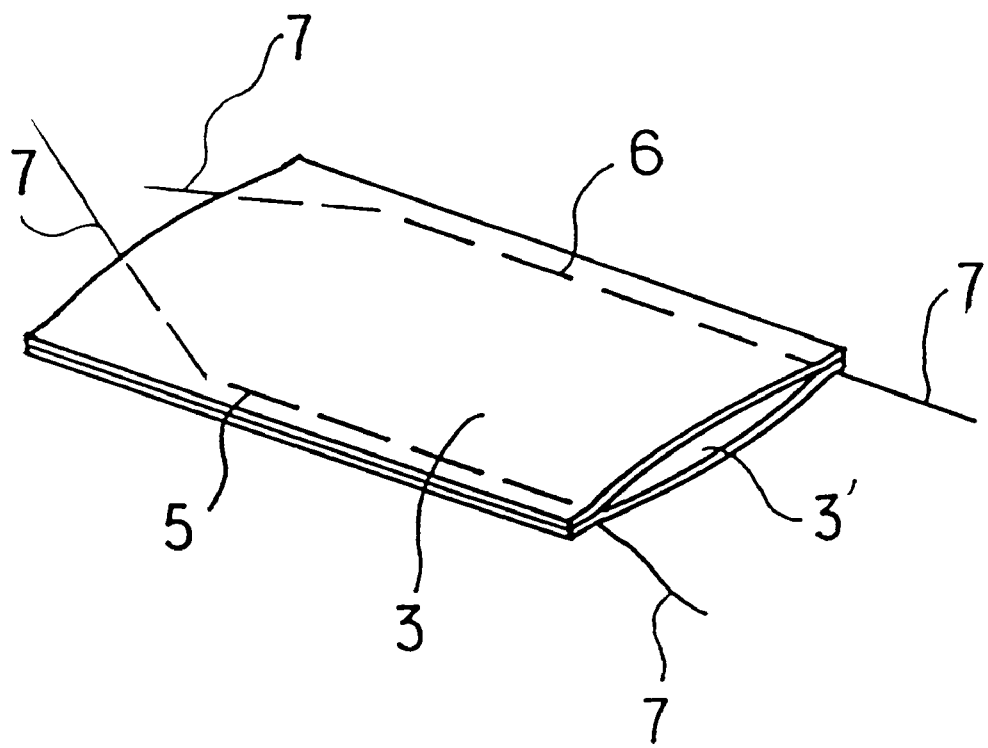
FIG. 7 demonstrates another embodiment of supporting element for staple region made of bioabsorbable polymer as a whole, wherein plain stitch with sewing yarn is diagonally placed in one end section to narrow an opening of the supporting element at the end.

FIG. 7 discloses another supporting element for staple region of the invention. The supporting element comprises unwoven fabrics (3), (3') made of biodegradable and bioabsorbable material, which are integrated together at both selvage in middle section and one end section by stitching up with sewing yarns (5), (6). In the other end section, sewing yarns are diagonally placed from selvage to near center position of the end to narrow an opening of the supporting element at the end. When the supporting element of FIG. 7 is applied to said double staple-type automatic stapling device (8) shown in FIG. 2, the narrowed end of supporting element is retained at the tip of cartridge section (9) without misregister and frame section (10) leading to inhibition of turnup of the supporting element.

Figure 8:
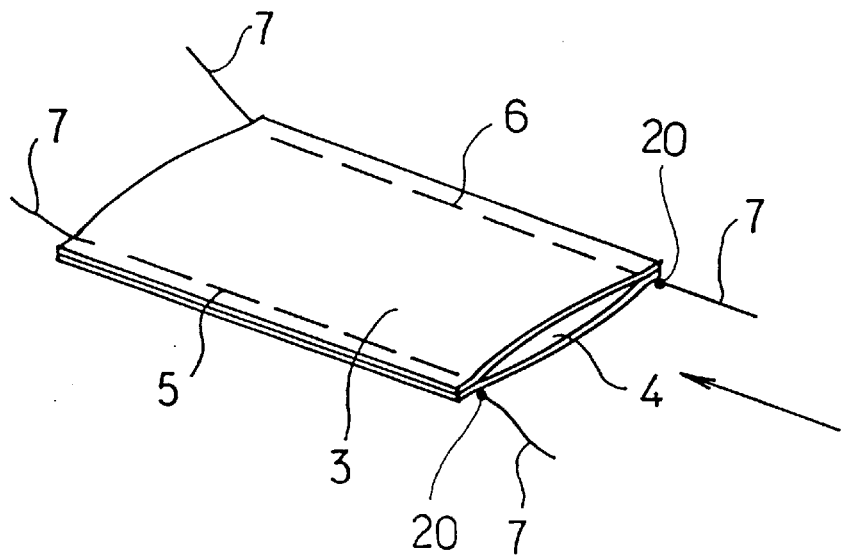
FIG. 8 is a diagonal view showing another embodiment of supporting element for staple region of the invention.

As shown in FIG. 8, a knot (20) may be formed so as to inhibit separation of unwoven fabric (3) and stretch warp knit (4). The knot maintaining plain stitch with sewing yarns (5), (6) makes it easier to cut unwoven fabric (3) on the dirrection as indicated by the arrow.

Figure 9:
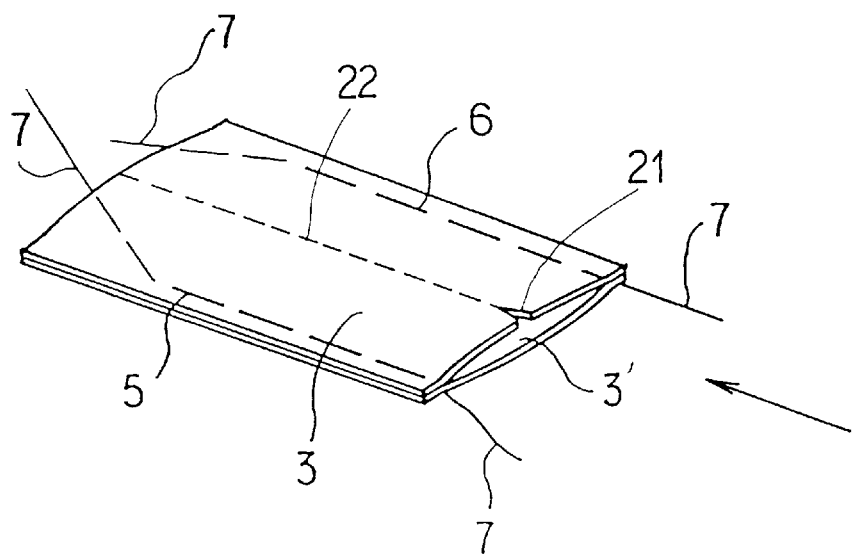
FIG. 9 is a diagonal view showing another embodiment of supporting element for staple region of the invention.

As shown in FIG. 9, notch (21) and/or perforation (22) may be formed on the centerline of the unwoven fabric (3) to cut unwoven fabric (3) with cutter easily along notch (21) and/or perforation (22). Other means to facilitate cutting of unwoven fabric (3) are temporary sewing or adhesion to form region with poor strength; and resin treatment or hot press to form paper-like region.

Figure 10:
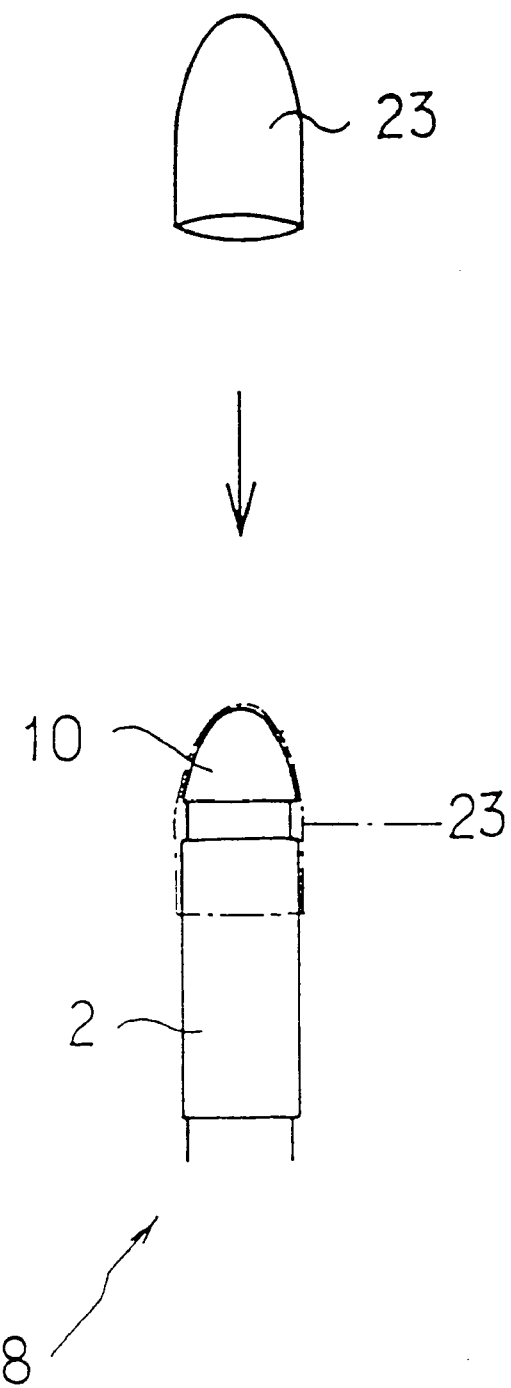
FIG. 10 is a sectional view showing another embodiment of supporting element for staple region of the invention with protective cap.

As shown in FIG. 10, a protective cap (23) is put on frame section (10) fitted with the supporting element (2) so as to prevent turnup or misregister of the supporting element (2) fitted, when frame section (10) is placed under the body tissue to be cut.

The protective cap (23) may be put on cartridge section (9), when cartridge section (9).

The protective cap (23) may be formed as tube-like body composed of knit or woven fabric, unwoven fabric, plastic film, etc. The shape of protective cap is preferably adjusted to the tip shape of automatic stapling device (8).

The same results as above were obtained by using sewing thread composed of polyester in place of suture as sewing yarn.

Example 2

Figure 5:
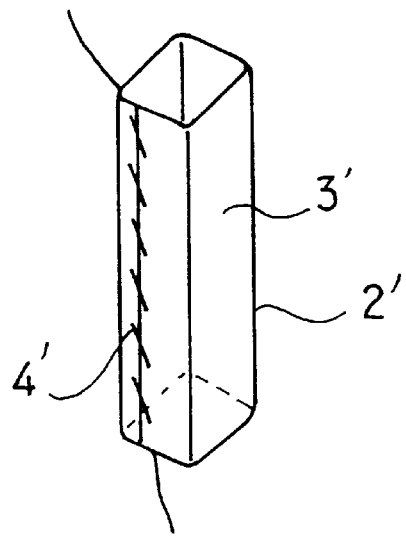
FIG. 5 demonstrates a supporting element for staple region made of bioabsorbable polymer as a whole.
Figure 6:
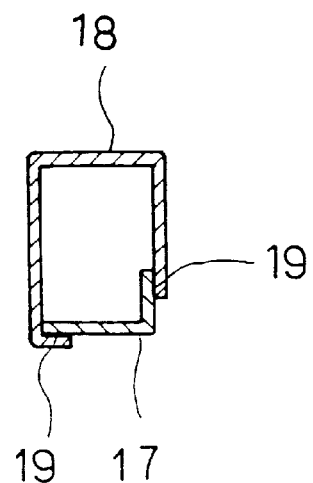
FIG. 6 demonstrates a supporting element for staple region made of bioabsorbable polymer only at a peripheral region fixed by staples.

FIG. 5 shows the supporting element for staple region of the invention II. The supporting element (2') comprises above-mentioned unwoven fabric (3') made of polyglycolic acid. Both ends of unwoven fabric are integrated together by plain stitch with suture (4'). As shown in FIG. 6, the supporting element (2') may have unwoven fabric (17) made of bioabsorbable polymer at a peripheral region fixed by staple. The unwoven fabric (17) is attached to low-cost unwoven fabric (18) which is not made of biodegradable and bioabsorbable material with adhesive (19).

The supporting element for staple region of the invention II may be employed in the same manner as said supporting element of the invention I shown in example 1.

The supporting element for staple region of the invention is characterized in that the supporting element prevents air leakage from section cut and rupture of soft tissues, that stretch of streachable material attached to fabric-like object facilitates fitting the supporting element on a variety in size of automatic stapling devices or adjusting position of the supporting element and that tension of the stretchable material prevents misregister after fitted and facilitates cutting operation after fixation by staple. The supporting element is also ecomonical because of small proportion of expensive biodegradable and bioabsorbable material. The unwoven fabric made of biodegradable and bioabsorbable material may be combined with low-strechable fabric when strechable sewing yarn is employed.

What is claimed is:

1. A supporting element for staple region comprising a fabric-like object having a tube-like shape with two open ends, said supporting element in one end having a narrowed opening formed by stitching up that open end with sewing yarn.

2. A tube-like supporting element for staple region according to claim 1 comprising a fabric-like object made of biodegradable and bioabsorbable material integrated with stretchable textile at both ends.

3. The tube-like supporting element for staple region according to claim 2 wherein said material and said textile are integrated with sewing yarn in plain stitch and ends of the sewing yarn extend to the exterior of the supporting element.

4. The tube-like supporting element for staple region according to claim 2 wherein said biodegradable and bioabsorbable material is at least one selected from the group consisting of polyglycolic acid, polylactic acid, copolymer of polyglycolic acid and polylactic acid, mixture of polyglycolic acid and polylactic acid, para-dioxanone, polycaprolactone and chitin.

5. A tube-like supporting element for staple region according to claim 2 wherein stretchable textile is stretch warp knit.

6. A tube-like supporting element for staple region according to claim 2 wherein said unwoven fabric is made of polyglycolic acid.

7. A method for cutting an affected part comprising the steps of;
   (1) fitting tube-like supporting elements for staple region comprising a fabric-like object having a tube-like shape on frame section and staple built-in-type cartridge section respectively;
   (2) sandwiching a disordered tissue in the body having affected part and normal part between the frame section and the cartridge section;
   (3) integrating the tissue with the fabric-like object made of biodegradable and bioabsorbable material;
   (4) separating an affected part from a normal part; and
   (5) removing stretchable textile.

8. A method for cutting an affected part comprising the steps of;
   (1) fitting tube-like supporting elements for staple region according to claim 6 on frame section and staple built-in-type cartridge section respectively;
   (2) sandwiching a disordered tissue in the body having an affected part and a normal part between the frame section and the cartridge section;
   (3) integrating the tissue and the fabric-like object made of biodegradable and bioabsorbable material; and
   (4) separating the affected part from the normal part.

* * * * *